US 6,549,687 B1

(12) United States Patent
Kochergin et al.

(10) Patent No.: US 6,549,687 B1
(45) Date of Patent: Apr. 15, 2003

(54) SYSTEM AND METHOD FOR MEASURING PHYSICAL, CHEMICAL AND BIOLOGICAL STIMULI USING VERTICAL CAVITY SURFACE EMITTING LASERS WITH INTEGRATED TUNER

(75) Inventors: Vladimir Kochergin, Westerville, OH (US); Philip Swinehart, Westerville, OH (US)

(73) Assignee: Lake Shore Cryotronics, Inc., Westerville, OH (US)

( * ) Notice: Subject to any disclaimer, the term of this patent is extended or adjusted under 35 U.S.C. 154(b) by 0 days.

(21) Appl. No.: 09/983,999

(22) Filed: Oct. 26, 2001

(51) Int. Cl.[7] .............................. G02B 6/00; G01B 9/10; H01S 3/10
(52) U.S. Cl. ..................... 385/12; 372/20; 250/227.27
(58) Field of Search .............................. 385/12, 18, 24; 372/6, 20, 32, 45, 96, 98, 99, 107; 356/32; 250/227.11, 227.12, 227.27, 226

(56) References Cited

U.S. PATENT DOCUMENTS

| | | |
|---|---|---|
| 4,761,073 A | 8/1988 | Meltz et al. |
| 4,778,987 A | 10/1988 | Saaski et al. |
| 5,202,939 A | 4/1993 | Belleville et al. |
| 5,291,502 A | 3/1994 | Pezeshki et al. |
| 5,359,681 A | 10/1994 | Jorgenson et al. |
| 5,380,995 A | 1/1995 | Udd et al. |
| 5,401,956 A | 3/1995 | Dunphy |
| 5,629,951 A | 5/1997 | Chang-Hasnain et al. |
| 5,771,253 A | 6/1998 | Chang-Hasnain et al. |
| 5,815,278 A | 9/1998 | Johnston et al. |
| 6,024,488 A | 2/2000 | Wu et al. |
| 6,122,305 A | 9/2000 | Putnam et al. |
| 6,141,098 A | 10/2000 | Sawatari et al. |
| 6,204,920 B1 | 3/2001 | Ellerbrock et al. |
| 6,233,263 B1 * | 5/2001 | Chang-Hasnain et al. .... 372/32 |
| 6,301,274 B1 * | 10/2001 | Tayebati et al. ............... 372/20 |
| 6,438,149 B1 * | 8/2002 | Tayebati et al. ............... 372/45 |

OTHER PUBLICATIONS

Coldren, Larry A., "Monolithic Tunable Diode Lasers," *IEEE Journal on Selected Topics in Quantum Electronics*, vol. 6, No. 6, pp. 988–999 (Nov./Dec. 2000).

Harris, James S., "Tunable Long–Wavelength Vertical–Cavity Lasers: The Engine of Next Generation Optical Networks?," *IEEE Journal on Selected Topics in Quantum Electronics*, pp. 1145–1160, vol. 6, No. 6 (Nov./Dec. 2000).

Chow, Weng W. et al., "Design, Fabrication, and Performance of Infrared and Visible Vertical–Cavity Surface–Emitting Lasers," *IEEE Journal of Quantum Electronics*, pp. 1810–1824, vol. 33, No. 10 (Oct. 1997).

Chang–Hasnain, Connie J. et al., "MEMS cantilevers precisely adjust cavity thickness to yield broadly tunable VCSELs" *OE Magazine*, The Monthly Publication of SPIE—The International Society for Optical Engineering (May 2001).

(List continued on next page.)

*Primary Examiner*—Akm E. Ullah
*Assistant Examiner*—Tina M Lin
(74) *Attorney, Agent, or Firm*—Nixon & Vanderhye P.C.

(57) ABSTRACT

An optical sensor diagnostic system utilizing a tunable Vertical Cavity Surface Emitting Laser (VCSEL) that incorporates an integrated MEMS tuning mechanism provides variable wavelength light into an optical fiber with improved wavelength scanning speed and greater simplicity of construction. Sensors, such as Bragg gratings, are disposed along the fiber in the light path. Each sensor reflects or transmits light exhibiting a characteristic amplitude feature with respect to wavelength, the wavelength position of which is affected by an environmental stimulus imposed thereon. The power of the reflected light is converted to an electrical signal by a simple detector and monitored by circuitry that detects changes in reflected power and provides output signals indicative of the environmental stimulus for each sensor.

51 Claims, 5 Drawing Sheets

OTHER PUBLICATIONS

Data sheet, MetroFlex Tunable Optical Transmitters, 2 pages (Jul. 26, 2001).

News release, "Bandwidth9 Unveils Industry's First VCSEL–Based, Tunable Optical Transmitter Module for Metro DWDM Applications" (Jan. 4, 2001).

News release, "Bandwidth9 Announces Plans to Develop MetroFlex™ Tunable Optical Filters for Use in DWDM Metropolitan Area Networks" (Feb. 8, 2001).

Press Releases listing, http://www.bw9.com.

Vakhshoori, D. et al., "2mW CW singlemode operation of a tunable 1550 nm vertical cavity surface emitting laser with 50 nm tuning range," *Electronics Letters*, vol. 35 No. 11, pp. 900–901 (Mar. 27, 1999).

Larson, M.C. et al., "Wide and continuous wavelength tuning in a vertical–cavity surface–emitting laser using a micromachined deformable–membrane mirror," *Appl. Phys. Lett.* 68(7), pp. 891–893 (Feb. 12, 1996).

Archambault, Jean–Luc et al., "Fiber Gratings in Lasers and Amplifiers," *Journal of Lightwave Technology*, vol. 15, No. 8, pp. 1378–1390 (Aug. 1997).

Duck, G., et al., CWF68 "High resolution and high speed distributed in–fiber Bragg grating strain measurements," Wednesday Afternoon, CLEO'99, pp. 295–296 (May 26, 1999).

Chang–Hasnain, Connie J., "Tunable VCSEL," *IEEE Journal on Selected Topics in Quantum Electronics*, vol. 6, No. 6, pp. 978–987 (Nov./Dec. 2000).

Chan, C.C., et al., "Investigation of unwanted interferometric signals ina fiber Brag grating sensor using a tunable laser and a first derivative interrogation technique," *Optics Communications*, pp. 203–210 (Jan. 1, 2000).

Ball, G.A., et al., "Fiber Laser Source/Analyzer for Bragg Grating Sensor Array Interrogation," *Journal of Lightwave Technology*, vol. 12, No. 4 pp. 700–703 (Apr. 1994).

Measures, R.M. et al., "Tunable laser demodulation of various fiber Bragg grating sensing modalities," *Smart Mater., Struct.* 7, pp. 237–247 (1998).

Chan, Chi Chiu, et al., "Performance Analysis of a Time––Division–Multiplexed Fiber Bragg Grating Sensor Array by Use of a Tunable Laser Source," *IEEE Journal of Selected Topics In Quantum Electronics*, vol. 6, No. 5, pp. 741–749 (Sep./Oct. 2000).

Hsu, Kevin, "Continuously Tunable Photopumped 1.3– m Fiber Fabry–Perot Surface–Emitting Lasers," *IEEE Photonics Technology Letters*, vol. 10, No. 9, pp. 1199–1201 (Sep. 1998).

\* cited by examiner

SYSTEM AND METHOD FOR MEASURING PHYSICAL, CHEMICAL AND BIOLOGICAL STIMULI USING VERTICAL CAVITY SURFACE EMITTING LASERS WITH INTEGRATED TUNER

CROSS-REFERENCES TO RELATED APPLICATIONS

Not applicable.

STATEMENT REGARDING FEDERALLY SPONSORED RESEARCH OR DEVELOPMENT

Not applicable.

FIELD OF THE INVENTION

This invention relates to systems using vertical cavity, surface emitting lasers (VCSELs) having integrated MEMS (micro-electromechanical) wavelength tuner to interrogate optical sensors, including fiber and planar Bragg gratings, etalons, characteristic absorption or reflection sensors such as bandgap semiconductors and surface plasmon resonance sensors sensitive to physical, chemical and biological stimuli and, more particularly, to specific system configurations for use with such Bragg grating, etalon, absorption/reflection and surface plasmon resonance sensing devices.

BACKGROUND OF THE INVENTION

Fiber optic sensors employing measurements of the shift of wavelength position of a sensor spectral peculiarity (maximum, minimum, slope or some other function) under the influence of a physical stimulus are well known to those skilled in the art. The examples of such sensors include Bragg grating-based strain, pressure, temperature and current (via the associated magnetic fields) sensors, surface plasmon resonance (SPR) biological and chemical sensors, semiconductor absorption band-edge based fiber-optic sensors and Fabry-Perot (FP) etalon pressure, temperature and sensors. The utilization of such sensors has been retarded in the marketplace because of many well known problems, including the susceptibility of simple, inexpensive sensing systems to optical noise and the great expense of most of the solutions found to overcome said susceptibility. It will be revealed that combining a new type of laser, a vertical cavity, surface emitting laser (VCSEL) with an integrated micro-electromechanical (MEMS) tuning mechanism, as an interrogating instrument with sensors of many different types will enable new, less expensive and more reliable class of optical sensor systems.

A Bragg grating is a series of optical elements that create a periodic pattern of differing indices of refraction in the direction of propagation of a light beam. A Bragg grating is formed in an optical fiber by means of exposing ultraviolet sensitive glass (usually germanium doped fiber) with an ultraviolet (UV) beam that varies periodically in intensity, usually accomplished by means of an interference pattern created by a phase mask or split beam, such as with a Lloyd's mirror apparatus. Planar Bragg gratings are created by exposing a "photoresist" of any of a number of types through a phase shift or other type of mask, or they can be written directly with an electron beam. Light reflections caused by the periodic index of refraction pattern in the resulting grating interfere constructively and destructively. Since the refractive index contrast between UV-exposed and unexposed sections of fiber is small but the number of sections is very large, the reflected beam narrows its spectrum to a very sharp peak, as narrow as a fraction of a nanometer in spectral width. It can also be arranged by means of a phase shift design that the reflected peak can contain within it an even narrower "valley" of absorption, as narrow as a few picometers in spectral width. Conversely, the transmitted portion of the light beam exhibits complimentary spectral power characteristics, i.e., a broader valley with a narrower peak within it.

It is known that Bragg gratings patterned into optical fibers or other waveguides may be used to detect physical stimuli caused by various physical parameters, such as, for example, strain, pressure, temperature, and current (via the associated magnetic fields) at the location of the gratings, such as is described in U.S. Pat. Nos. 4,806,012 and 4,761,073 both to Meltz, et al; U.S. Pat. No. 5,380,995 issued to E. Udd; U.S. Pat. No. 6,024,488 issued to J. Wu; and the publication authored by Kersey, A. D., et.al. [10$^{th}$ Optical Fiber Sensors Conference, Glasgow, October 1994, pp. 53–56]. Generally, in such a sensor, the core and/or cladding of the optical fiber (or planar waveguide) is written with periodic grating patterns effective for selectively reflecting a narrow wavelength band of light from a broader wavelength band launched into the core (waveguide layer in the waveguide). The spectral positions of sharp maxima or minima in the transmitted and reflected light intensity spectra indicate the intensity of strain, temperature, pressure, electrical current, or magnetic field variations at the location of the grating. The mechanism of the spectral position changes lies in changes either the in grating period or the indices of refraction, or both, which can be affected by various environmental physical stimuli, such as temperature and pressure. Frequently, more than one stimulus or physical parameter affects the sensors at the same time, and compensation must be designed into the sensor or the measurement technique for all the variables but one, which can be accomplished by many physical, optical and electronic techniques known in the art. The typical sensitivity limits of fiber grating sensors in the current art are about 0.1° C. and/or 1 microstrain, respectively. Advantages of a spectral shift method of sensor interrogations include the high accuracy of wavelength determination (akin to the advantages of measuring electrical frequency instead of magnitude) and immunity to "optical noise" due to fluctuations in fiber transmission amplitude (microbending losses, etc.). It also allows the multiplexing of many sensors on the same fiber via wavelength dependent multiplexing techniques (WDM), e.g., dividing the total wavelength band into sections dedicated to individual sensors.

The precision, dynamic range and multiplexing capabilities of the all optical sensor interrogation techniques are defined in part by the spectral power of the light source, especially in cases in which a broadband source is used. The LEDs, SLDs (superluminescent diodes) and various lamps usually used provide spectral power that can be too little when divided into nanometer-sized segments. This limits critical parameters such as the magnitude of the reflected peak available to the optical sensor, causing lower than desirable signal to noise ratios. Another technique, the use of a conventional laser diode tuned with motorized external cavity, electrical current or temperature mechanisms is more effective because all the power of the laser is contained in a narrow beam as it is tuned across the spectrum. Several techniques have been proposed: see for example Froggatt, (U.S. Pat. No. 5,798,521); the use of a conventional laser diode tuned with electrical current has been proposed by Dunphy et. al. (U.S. Pat. No. 5,401,956); and the use of a tunable fiber laser has been proposed by G. A. Ball et. al. [J. of Lightwave Technology, vol. 12, no. 4, April 1994 p 700]. When using a scanning laser technique, an inexpensive detector and electronics system simply determines the wavelength at the peak (or null) of the reflected (or transmitted) light intensity against a known wavelength reference. However, past art approaches are generally too expensive, too slow, too unstable or too inaccurate to have a wide range of practical applications. Laser diodes tuned with current, while inexpensive and faster than thermal methods, suffer from narrow tuning wavelength spans, which limits practical applications to only time division-multiplexed (TDM) Bragg sensors. Such lasers are completely unusable in surface plasmon or semiconductor absorption edge shift sensors. The broadband light source method utilizes an inexpensive light source, but requires a spectrometer to read the signals (an optical spectrum analyzer may cost as much as $35,000). It is most practical when many sensors are multiplexed on the same fiber. Still, spectrometers are temperamental and not well suited to field use. The lasers tuned with external cavities that are now in use, on the other hand, typically are more expensive than spectrometers, but have the advantage of using an inexpensive detector. In addition, such lasers are typically slow to tune, such as 100 nm/sec, and may be even more delicate than spectrometers. Scanning (or tuning) speed is especially important in applications in which absorption and polarization related noise are significant because of negative effects on the signal to noise ration (SNR). Mass produced MEMS-tunable VCSELs, configured as sensing instruments, are expected to cost at least an order less than prior art lasers and be at least two orders of magnitude faster than prior art lasers.

Surface plasmon resonance-based sensors for biological and/or chemical monitoring are well known to those skilled in the art. Surface plasmon waves are electromagnetic waves that may exist at the boundary between a metal and a dielectric (hereinafter referred to as the "sample"). Such waves can be excited by light that has its electric field polarized parallel to the incident plane (i.e., transverse magnetic (TM) polarized). When the parallel component of the propagation constant of the incident light equals the real part of the surface plasmon wave propagation constant, the incident light resonantly excites the surface plasmon waves, and a fraction of the incident light energy is transferred or dispersed to surface plasmon resonance (SPR). This dispersion of energy depends on both the dielectric constant of the metal and that of the sample in contact with the metal. By monitoring the resonance wavevector of the metal/sample interface, the dielectric constant of the sample (gas or solution) may be obtained. Alternatively, if the sample is contaminated by a chemical species, dielectric constant measurements may provide the concentration of the chemical species in the sample. The typical SPR spectral minimum is at least two orders of magnitude wider than the typical Bragg grating minimum or maximum.

Traditionally, SPR has been measured using the Kretschmann configuration (Kretschmann and Raether, Z. Naturforsch. Teil A 23:2135–2136, 1968). In this configuration, a thin layer of highly reflective metal (such as gold or silver) is deposited on the base of a prism. The metal surface is then contacted with the sample, and the SPR reflection spectra of the sample is measured by coupling TM polarized, monochromatic light into the prism and measuring the reflected light intensity as a function of the angle of incidence. The angle of minimum reflective intensity is the resonance angle at which maximum coupling occurs between the incident light and the surface plasmon waves. This angle, as well as the half-width of the resonance spectrum and the intensity at the angle of minimum reflective intensity, may be used to characterize or sense the sample that is in contact with the metal surface (Fontana et al., Applied Optics 27:3334–3339, 1988).

Optical sensing systems have been constructed based on the Kretschmann configuration described above. Such systems utilize the sensitivity of SPR to changes in the refractive indices of both bulk and thin film samples, as well as to changes in the thickness of thin films. These systems, in conjunction with appropriate chemical sensing layers, have led to the development of a variety of SPR-based chemical sensors, including immunoassay sensors (e.g., Liedberg et al., Sensors and Actuators 4:299–304, 1983; Daniels et al. [Sensors and Actuators 15:11–17, 1988]; Jorgenson et al., [IEEE/Engineering Medicine and Biology Society. Proceedings 12:440–442, 1990]), gas sensors (e.g., Liedberg et al., ibid, Gent et al., [Applied Optics 29:2843–2849, 1990]), and liquid sensors (e.g., Matsubaru et al., [Applied Optics 27:1160–1163, 1988]). An SPR sensor usually utilizes the wavelength of minimum amplitude as a function or angle of reflection. However, the shape of the minima can be modified if an additional polarizer and phase plate (or retarder) are introduced between the sensor and detector at some predetermined angle with respect to the polarization of light illuminating the SPR sensor (Homola J., et al, Sensors and Actuators B, B51 (1–3), Augsut 1998, p.331, Kabashin A. V et al, Sensors and Actuators B, B54 (1–2), January 1999, p.51). This modification is due to phase and polarization peculiarities near the surface plasmon resonance excitation conditions. Moreover, minima can be transformed into maxima (Homola, ibid), which has the potential for increasing the resolution of SPR sensors While the Kretschmann configuration for SPR-based chemical sensors offers significant sensitivity, their relatively large size has severely restricted their application. An optical fiber sensor that utilizes SPR to detect a material in contact with the sensor and utilizes incident light having multiple wavelengths as the excitation energy is described by Jorgenson, et al. (U.S. Pat. No. 5,359,681). While being small and considerably less expensive than the non-waveguide optical sensor, it is at least an order of magnitude less sensitive. The reason for this drop in sensitivity is obvious—in a non-waveguide optical scheme with 5000 pixels, the SPR minimum is read by at least 2000 pixels. However, in the fiber optic scheme with a spectrometer as a readout instrument (wavelength resolution not better than 0.1 nanometer and SPR minimum spectral width around 60 nm) the SPR minimum will be characterized by 600 pixels at most, leading to less precise interpolations to locate the minimum, and hence changes in the wavelength position of the minimum. Conversely, the use of inexpensive tunable lasers with sub-nm wavelength resolution as light sources in fiber systems will eliminate the expensive spectrometer and yield precision at least comparable to that of the non-waveguide optical system. The illustrative problem that arises in the broadband light source/spectrometer configuration, specifically a lack of optical intensity per measurement point, has, in the case of SPR sensors, the additional undesirable attribute of overheating of the sensor. If the total light intensity of the broadband light source is increased to compensate for the small intensity available to each pixel in the spectrometer charge coupled device (CCD) array, overheating of the SPR sensor will occur because approximately half the incident light is dissipated in heat in the metal layer whether it contributes to the usable signal or not. Heating is not only harmful to the biological and/or chemical sample under test, but also can induce refractive index changes in the fiber and/or sample, causing much larger variations in the SPR wavevector than the perturbation to be detected. Very fast tuning lasers, having very narrow emission spectra, are ideal to address this problem, since the total intensity illuminating the sensor at any given time will be almost exactly equal to the intensity of the reflected light available to detect the change in stimulus.

An illustrative example of a characteristic absorber/reflector material is a semiconductor. A semiconductor means that comprises an optical sensor with optical-wavelength-dependent characteristics that may vary as a function of a physical parameter such as temperature is well known to those skilled in the art (see, for example patent, issued to Christenson (U.S. Pat. No. 4,136,566) or Quick et al. (U.S. Pat. No. 4,355,910). The optical-wavelength-dependent characteristic (semiconductor absorption band edge) is usually monitored by present art methods in one wavelength band, in which case measurements are intensity-dependent, or in two wavelength bands, after which a ratio of intensities is taken. In both cases, the sensitivity and accuracy of such sensor systems are low and more-or-less sensitive to optical noise (microbending, etc.). Scanning very rapidly through the whole semiconductor transmission intensity slope related to the forbidden band edge using a tunable VCSEL with high wavelength resolution will provide the opportunity for mathematical enhancement of the sensitivity of such sensors by at least in order of magnitude. Broadband light source/spectrometer configurations are not suitable for reasons similar to those described in [0011]. The high total illumination intensity will cause self-heating of the sensor, which is crucial especially for temperature sensors. Reducing the illumination intensity, on the other hand, will cause uncertainty due to photodetector dark noise and other sources of optical noise.

Fiber etalon-based sensors are well known to those skilled in the art (see, for example, U.S. Pat. No. 5,646,401 issued to E. Udd). Etalons consist of two mirrored surfaces that may be internal or external to the opticl fiber. The reflectivity of an etalon is defined by interference between light waves reflected from first and second mirrors. The advantages of etalon-based pressure, temperature and/or stain sensors include the low cost of etalons and very high sensitivity. However, with broadband light sources used for interrogation, measurements that are intensity based or count interference fringes are very susceptible to optical noise or other technical problems (e.g., losing count of the fringes), to the point of being impractical. The sole practical, self-calibrating system uses an optical cross-correlating interferometer as a detector, also an expensive technique (see, for example, U.S. Pat. Nos. 5,202,939 and 5,392,117 both issued to Belleville, et al.).

A new kind of laser, a vertical cavity surface emitting laser (VCSEL), has recently been invented. Generally, VCSELs are made completely with wafer-level processing and the chips emit from the direction of the broad surface of the wafer, rather than having to be cleaved out of the wafer in order to have an exposed p-n junction edge from which to emit, as in older art. This enables another benefit to be designed into the wafer structure—tunability. This is done with micromachining (MEMS) technology by placing a stack of optical layers, forming a mirror, in front of the emitting surface in such a way that the stack can be varied in its distance from the emitting surface by piezoelectric, magnetic, electrostatic or some other micro-actuating means. The groups of C.J. Chang-Hasnain (U.S. Patent, [IEEE J. on Selected Topics in Quantum Electronics, V 6, N 6, November 2000, p. 978]), J. S. Harris Jr. (U.S. Pat. No. 5291502, [Appl. Phys. Lett. 68 (7), February 1996 p. 891]), and Vakhshoori [Electronics Letters, May 1999, V. 35, N. 11 p. 900] have shown the potential for making tunable VCSELs with MEMS tuning mechanisms with wide tuning ranges and fast tuning speeds. Tunable VCSELs are relatively simple to manufacture, exhibit continuous mode-hop-free tunability over a wide spectrum, and potentially offer orders of magnitude lower cost as compared to prior art tunable lasers or optical spectrometers. Integrated, MEMS-tunable VCSELS make possible truly affordable and accurate optical sensor systems by combining low cost detectors and low cost excitation sources, one or the other of which is very expensive in the prior art systems with the accuracy and resolution to be viable commercially. In addition to the orders of magnitude lower cost of source/detector combinations, lower cost sensor will become available because of the orders of magnitude greater tuning speed.

BRIEF SUMMARY OF THE INVENTION

The present invention provides a means of optical wavelength scanning Bragg grating, characteristic absorber/reflector, etalon and surface plasmon resonance sensors of all types with integrated, MEMS-tunable VCSELs in order to measure various physical parameters at several orders of magnitude lower cost than prior art, with the added benefits of enhanced accuracy, ruggedness and reliability.

In more detail, the present invention provides, as an illustrative embodiment, a diagnostic system which interfaces with optical fibers or optical waveguides having Bragg grating or other types of sensors as described herein, embedded therein for the determination of static and dynamic values of various physical, chemical or biological parameters, and, further, to provide means of guaranteeing wavelength accuracy during the scanning cycle.

In accordance with one aspect of a preferred illustrative embodiment of the invention, an optical sensor diagnostic system includes an integrated MEMS-tunable VCSEL for providing a wavelength-tunable light in response to a voltage or other control signal, the tunable light being launched into an optical waveguide. At least one optical sensor, disposed in the path of the tunable light, provides a reflected light having an associated local amplitude minimum, maximum or slope. The said local amplitude maximum could contain one or more local amplitude minimums inside said local amplitude maximum, while said local amplitude minimum could contain one or more local amplitude maximums inside said local amplitude minimum. The wavelength at said minimum, maximum or slope of amplitude varies in response to an environmental stimulus imposed upon the corresponding sensor. The tunable VCSEL individually illuminates each of the sensors throughout its associated wavelength band of an amplitude minimum, maximum or slope. An optical circulation device, disposed in the path of the tunable light between the tunable VCSEL and the sensors, isolates the tunable VCSEL from the reflected light and directs the reflected light from each of the sensors to the optical detector means, disposed for detecting the reflected light and for providing an electrical detection signal indicative of the power of the reflected light. A tuning controller provides a variable voltage or other signal to the tunable VCSEL indicative of the desired wavelength of the tunable light. A signal processor responsive to the electrical detection signal interprets a shift in the wavelength of the magnitude minimum, maximum or slope due to the environmental stimulus, and provides a signal indicative of said stimulus.

According to another aspect provided by an illustrative embodiment of the present invention, an optical sensor diagnostic system includes an integrated MEMS-tunable VCSEL for providing a wavelength-tunable light in response to a voltage or other control signal, the tunable light being launched into an optical waveguide. At least one optical sensor, disposed in the path of the tunable light, provides a transmitted light having an associated local amplitude minimum, maximum or slope. The said local amplitude maximum could contain one or more local amplitude minimums inside said local amplitude maximum, while said local amplitude minimum could contain one or more local amplitude maximums inside said local amplitude minimum. The wavelength at said minimum, maximum or slope of amplitude varies in response to an environmental stimulus imposed upon the corresponding sensor. The tunable VCSEL individually illuminates each of the sensors throughout its associated wavelength band of an amplitude minimum, maximum or slope. An optical isolation device, disposed in the path of the tunable light between the tunable VCSEL and the sensors, isolates the tunable VCSEL from the reflected light. The light transmitted through the said at least one optical sensor is directed by an out-going fiber to the optical detector means, disposed for detecting the transmitted light and for providing an electrical detection signal indicative of the power of the transmitted light. A tuning controller provides a variable voltage or other signal to the tunable VCSEL indicative of the desired wavelength of the tunable light. A signal processor responsive to the electrical detection signal interprets a shift in the wavelength of the magnitude minimum, maximum or slope due to the environmental stimulus, and provides a signal indicative of said stimulus.

In accordance with one aspect of a preferred illustrative embodiment of the invention, the said optical sensors are of reflective Bragg grating type. The sensors reflect light, having maxima or minima inside the maxima at a different reflection wavelength for each sensor, which vary their spectral positions due to an environmental stimulus, such as strain, pressure, temperature, electrical current or magnetic field imposed thereon.

In accordance with another aspect of a preferred illustrative embodiment of the invention, the said optical sensors are of transmittive Bragg grating type. The sensors transmit light, having minima or maxima inside the minima at a different transmission wavelength for each sensor, which vary their spectral positions due to an environmental stimulus, such as strain, pressure, temperature, electrical current or magnetic field imposed thereon.

In accordance with further aspect of a preferred illustrative embodiment of the invention, the said optical sensors are of reflective etalon type. The sensors reflect light, having maxima, minima or maxima and minima at a different reflection wavelength for each sensor, which vary their spectral positions due to an environmental stimulus, such as strain, pressure, temperature, electrical current or magnetic field imposed thereon.

In accordance with further aspect of a preferred illustrative embodiment of the invention, the said optical sensors are of transmittive etalon type. The sensors transmit light, having maxima, minima or maxima and minima at a different transmission wavelength for each sensor, which vary their spectral positions due to an environmental stimulus, such as strain, pressure, temperature, current or magnetic field imposed thereon.

In accordance with further aspect of a preferred illustrative embodiment of the invention, the said optical sensors are of reflective Surface Plasmon Resonance type. The sensors reflect light, having maxima or minima at a different reflection wavelength for each sensor, which vary in their spectral positions due to an environmental stimulus, such as temperature, biological or chemical stimuli imposed thereon.

In accordance with further aspect of a preferred illustrative embodiment of the invention, the said optical sensors are of transmittive Surface Plasmon Resonance type. The sensors transmit light, having maxima or minima at a different reflection wavelength for each sensor, which vary in their spectral positions due to an environmental stimulus, such as temperature, or biological and chemical stimuli imposed thereon.

In accordance with further aspect of a preferred illustrative embodiment of the invention, the said optical sensors are of a characteristic absorber/reflector type. Said characteristic absorber/reflector sensors, disposed in the path of the tunable light, provide a transmitted light having an associated local amplitude slope or local amplitude minimum, the wavelengths of which vary their spectral position due to an environmental stimulus, such as temperature, imposed thereon. This embodiment could be also realized in reflection mode, with multiple sensors coupled off the main fiber, if the reflective means is disposed in the light path such that the light is double-passed through the each of the sensors by means of a mirror and time domain multiplexing is utilized. In the case of an absorber/reflector exhibiting a minimum, wavelength division multiplexing can be utilized to the degree the width of the minimum allows as a fraction of the available tuning spectrum. The isolator in this realization of the present embodiment must be replaced by a circulator means.

The illustrative embodiments of the invention provide low cost, workable, practical diagnostic systems which function in cooperation with remote optical fiber sensor systems to measure static and dynamic strain, pressure, temperature, electrical currents and magnetic fields as well as acoustic or vibratory perturbations of items or structures and chemical and biological parameters. The remote sensors may be disposed on structures made of metal, plastic, composite, or any other materials that expand, contract, or vibrate, or the sensors may be embedded within such structures or immersed in liquids or gasses. The embodiments also provide a wavelength-tunable VCSEL, tunable smoothly and monotonically, and in particular, linearly or sinusoidally tunable with time. The embodiments further provide individual illumination of each sensor, thereby allowing all the tunable VCSEL power to be resident in a single narrow wavelength band at any instant in time. As a result, the reflected or transmitted light from each optical sensor has a high intensity, thereby providing a signal-to-noise ratio of such reflected or transmitted light that is much greater than systems that illuminate all sensors at the same time using a broadband source. Ultra-fine tuning of tunable VCSELs to a few parts per million will allow another order of magnitude increase in precision due to higher resolution and improved computational methods and statistical processing. The very low mass of the MEMS tuning mechanisms allow very high tuning speeds with very low hysteresis, providing the ability to average out optical noise in the sensor systems with many data points and allowing very close spacing of data in wavelength.

BRIEF DESCRIPTION OF THE DRAWINGS

The foregoing and other objects, features and advantages of the present invention will become more apparent in light of the following brief description of exemplary embodiments thereof as illustrated in the accompanying drawings, of which.

BEST MODES FOR CARRYING OUT THE INVENTION

Figure 1:
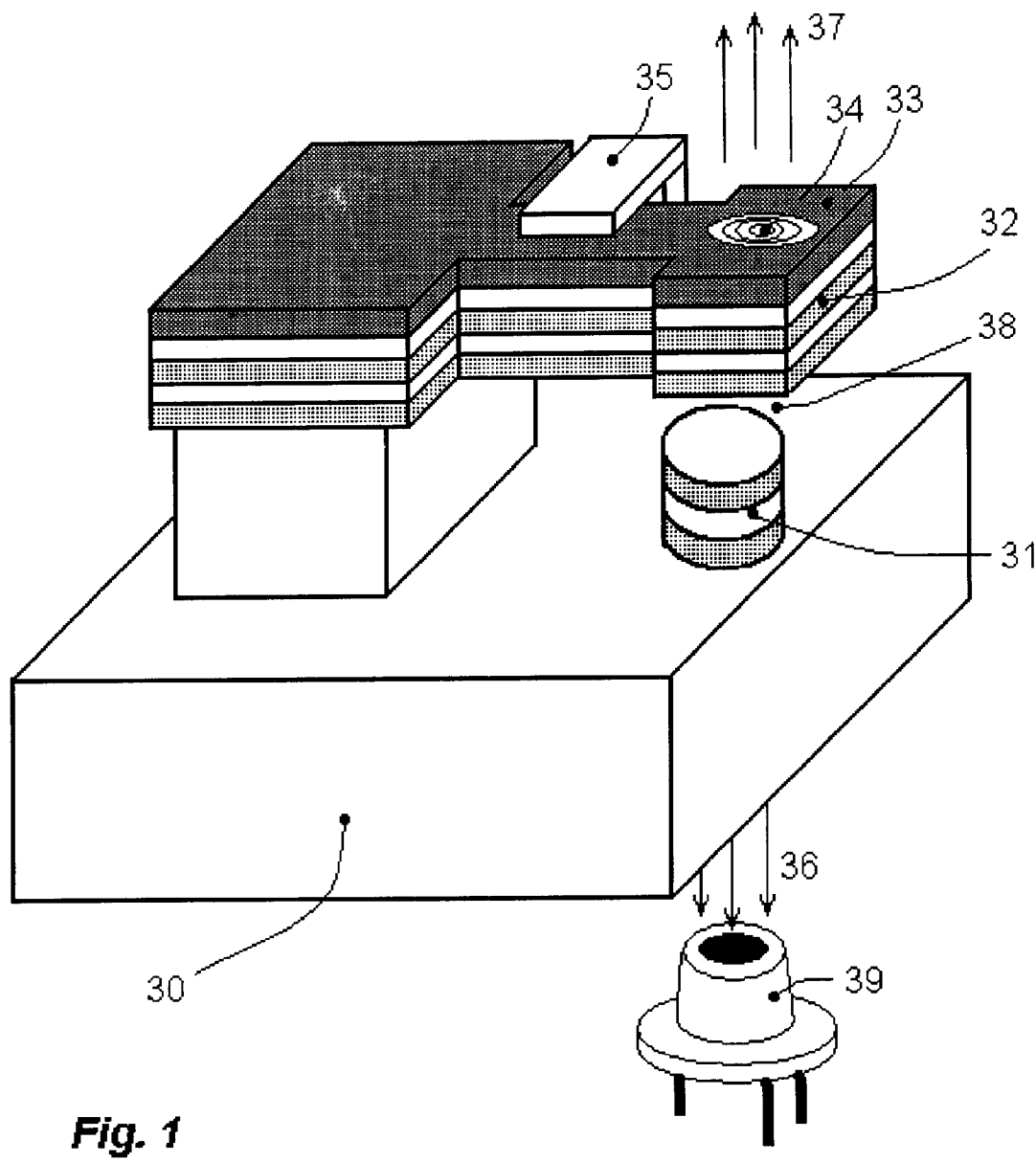
FIG. 1 is a schematic drawing of an illustrative VCSEL incorporating one example of an integrated MEMS (micro-electromechanical machined system) tuning mechanism in the form of a cantilevered mirror and optional lens.

FIG. 1 is an illustrative schematic drawing of a VCSEL incorporating one example of an integrated MEMS (micro-electromechanical machined system) tuning mechanism in the form of a cantilevered mirror and optional lens. Substrate chip 30 has fabricated upon it, when in wafer form, a multilayer stack of materials forming the light emitting VCSEL 31 and the tuning components consisting of mirror stack 32, actuator and structural means 33 that change the tuning cavity length 38, diffractive optical lens 34 (optional), capacitive cantilever position monitor 35 (optional) and light beams emitted in directions 36 and/or 37. If either mirror 32 or bottom of stack 31 is opaque, light is emitted only in one direction 37 or 36 respectively. Emission in both directions is possible if both 32 and 31 are partially transparent. This arrangement provides the simplest means for optical power monitoring with a photodiode 38 for the purpose of spectral power uniformity control. Electrical connections are not shown for simplicity.

Figure 2A:
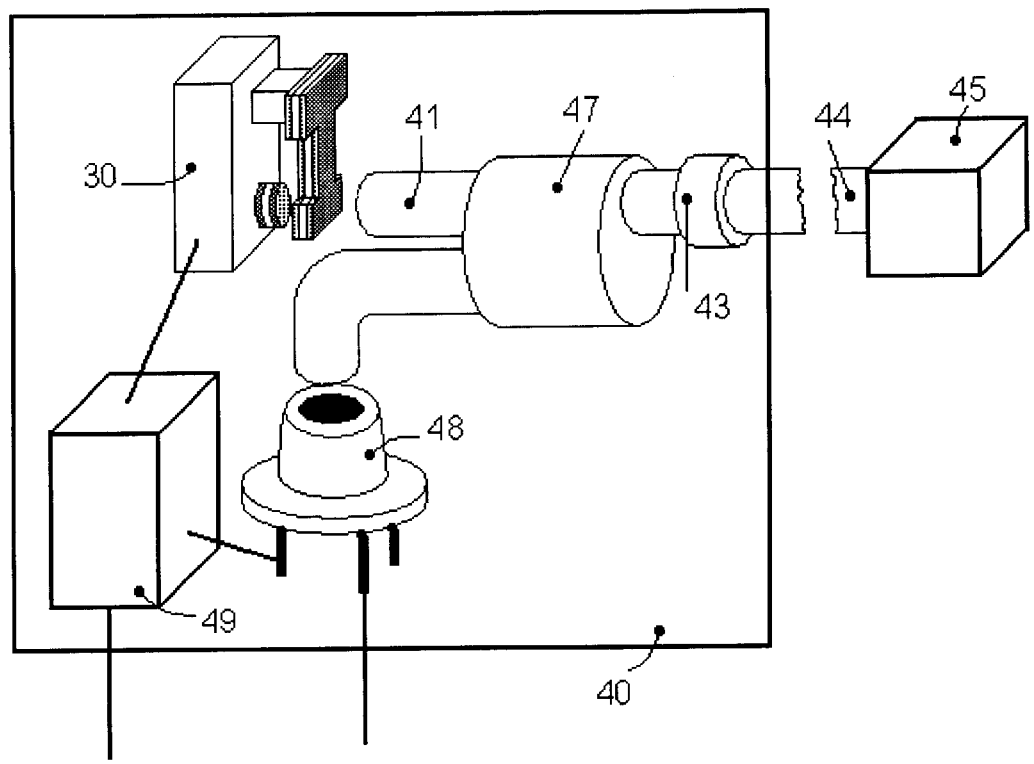
FIG. 2A is a schematic block diagram of a first state of an illustrative, exemplary non-limiting sensor diagnostic system capable of determining the value of static and dynamic physical, chemical or biological physical stimuli in a reflection mode employing a tunable VCSEL as an optical excitation source and a photodiode or similar simple device as a detector.

FIG. 2A shows an example illustrative embodiment of a diagnostic system 40 provided in accordance with one aspect of this invention. In more detail, FIG. 2A is a schematic block diagram of a first state of an illustrative, exemplary sensor diagnostic system capable of determining the value of static and dynamic physical, chemical or biological physical stimuli in a reflection mode employing a tunable VCSEL as an optical excitation source and a photodiode or similar simple device as a detector. Preferred embodiment diagnostic system 40 includes a MEMS-tunable VCSEL 30, a fiber light coupling means 41, an optical circulator 47, a wavelength reference 43, exterior fiber 44 and coupling means to the sensor or sensor array 45, a photodetector 48, and a control block 49. In said illustrative example, a tunable VCSEL 30 is assembled with necessary means to fiber couple 41 the emitted light, provide an accurate wavelength reference 43, and couple the VCSEL assembly 40 to an external fiber 44 to convey the laser light to an optical sensor or sensor array 45 in a reflection mode. A coupler or circulator 47 must be provided to divert the optical signal reflected from the sensor 45 to the photodetector 48, the electrical signal from which is relayed to the control block circuitry 49 and external electronic circuitry as required. A circulator also provides the function of isolating the VCSEL from back-reflected light. If a coupler is used to divert the light to the detector, a separate isolator must be incorporated between it and the laser. The control block 49 may or may not control the laser temperature via a thermoelectric element or other means and may or may not adjust the laser power output according to a signal from a monitor photodiode 38, as required.

In this embodiment, the tunable VCSEL 30 provides a wavelength-tunable light in response to a tuner control signal provided by control block 49. This tunable light provided by tunable VCSEL 30 is launched into an optical waveguide 44 such as an optical fiber. A sensor or sensor array 45, in this embodiment a Bragg grating sensor array, providing at least one optical sensor, is disposed in the path of the tunable light. The sensor array 45 includes individual Bragg gratings that each reflects light having different, non-overlapping, associated amplitude reflection maxima at individual reflection wavelengths, spectrally distinguishable one from the other. In the exemplary embodiment, the wavelength position of the amplitude maximum reflected by each of the Bragg gratings in the array 45 varies in response to a physical stimulus or perturbation imposed on the corresponding sensor.

The tunable VCSEL 30, by continuously scanning its output spectrum, individually illuminates each of the sensors in turn within the sensor array 45 in a wavelength band including the wavelength of maximum or minimum reflection associated with each sensor. An optical isolation and directing device such as optical circulator 47 is disposed in the path of the tunable light between the tunable VCSEL 30 and the sensor array 45. The circulator efficiently isolates the tunable VCSEL from light reflected by the sensor array 45 and diverts the reflected signals to a simple and inexpensive optical detector 48, such as a photodiode, disposed in the path of the light. The detector 48 provides an electrical detection signal indicative of the power of the reflected light that is directly related to the wavelength through the tuning control signal and the wavelength reference 43, if utilized. The series of optical signals obtained during a scanning cycle can contain one or more absorption or reflection bands from one or more wavelength reference devices 43 that can be incorporated for additional wavelength accuracy. Said reference signals do not change in wavelength position with any of the external stimuli measured by the sensors, and can be related in time to the tuning control signal.

Control block 49 responds to the electrical detection signal from the photodetector 48 in the example embodiment by calibrating a variable voltage or other tuning signal for the tunable VCSEL 30 to the wavelengths of the wavelength references, and providing said tuning signal to said VCSEL. Control block 49 may also include a signal processor responsive to the electrical detection signal for detecting a shift in the wavelength of maximum reflection due to a physical, chemical or biological stimulus on each of the sensors, and/or may cooperate with external circuitry to provide a signal indicative of the stimulus for each of the sensors. Control block 49 may also control the laser temperature by any of several known means and adjust the laser power to provide a constant power output with respect to wavelength using an independent monitor detector 38 (FIG. 1).

In more detail, referring to FIG. 2A, diagnostic system 40 includes a tunable VCSEL 30 which in this embodiment (FIG. 1) has a rear reflector stack of alternating quarter-wave layers of two different materials 31, the Fabry-Perot cavity region that contains the active material 31 (here a solid optical cavity), and an upper reflector 32, made as movable, suspended mirror layers with different indices of refraction of transparent material on a cantilever as illustrated, or, alternately, as a reflective or partially reflective single layer, such as aluminum. The relative position of the movable mirror structure with respect to the rest of the structure is changeable by the application of an electrostatic field or other control force, forming a variable optical cavity 38 (here an air or vacuum optical cavity). The mirror structure could be made in a form of a diaphragm suspended by other means by selective etching and release techniques, the relative position of which with respect to the rest of the structure is also changeable by the application of an electrostatic force, magnetic force or other force. The result of this is that the effective optical distance between the two reflectors making up the cavity 38 is adjustable. Since the resonant wavelength depends on this distance, the characteristic wavelength of the tunable VCSEL is continually tuned, for example, by varying the applied voltage and thereby the electrostatic field between the upper reflector and the remainder of the device.

It is desirable to provide energy within the tunable VCSEL 30 to achieve lasing. It should be noted that the energy could be provided by optical pumping means or by electrical pumping means (p-n or p-i-n junction). Although both methods are suitable for a sensor system, the electrically pumped embodiment is preferred from the point of view of lowest cost and greatest simplicity.

The operating wavelengths of the tunable VCSEL can be in the communication wavelength band (Chang-Hasnain [IEEE J. on Select. Topics in Quantum Electronics, V 6, N 6, November 2000, p. 978] Vkhshoori [Electronics Letters, may 1999, V. 35, N.11 p. 900]) or around 960 nm (J. S. Harris, [Appl. Phys. Lett. 68 (7), February 1996 p. 891]) or in any other desired band in which VCSELs are produced. When the distance between the tunable VCSEL 30 and a Bragg grating or other type of sensor 45 does not exceed about 1 km, many wavelength bands are usable. When this distance exceeds about 1 km, the losses may become too high at wavelengths not in the communications bands and tunable VCSELs 30 emitting within the communication wavelength bands may be more suitable.

A current control circuit within control block 49 (FIG. 2A) provides an electrical current to the tunable VCSEL 30, which controls the intensity of the output light. Adjusting the current through the diode (VCSEL active area 31) also causes slight changes in wavelength. However, this effect is not significant for this application. A pulsed current can be used to cause pulsed light, which would be required for Time Division Multiplexing (TDM) (although it should be noted that TDM could be realized by placing an electro-optical modulator anywhere between tunable VCSEL 30 and sensor array 45). In addition, a temperature control circuit could be used in the illustrative embodiment to provide a current drive to a thermoelectric (TE) cooler to stabilize the temperature of the tunable VCSEL 30 if needed. Other devices may be used to control the temperature if desired. A voltage control circuit can be used to control the electrostatic force between the movable reflector 32 and the active layers of the tunable VCSEL 31 and, by such means, can control the wavelength emitted by the tunable VCSEL in the illustrative embodiment. It should be noted that other control mechanisms than electrostatic can be used to position the VCSEL tuning mirror, and the tuning signal may or many not be a voltage.

In all exemplary embodiments, the tunable VCSEL 30 can provide a divergent output light beam to either the end plane of fiber 41, placed in close vicinity to the tunable VCSEL and perpendicular to the direction of emitted light propagation (butt-coupling method) or to a focusing lens, also represented by element 41, that provides focused light to optical fiber component isolator 42 or circulator 47. The lens may instead be a lens system that provides this function. The lens also could be realized as a diffractive element 34written photolithographically on the surface of the VCSEL mirror, adjacent to the fiber 41 or on the backside of the chip in the path of the light beam 36.

It should be noted that the optical circulator 47 may be replaced by an optical isolator 42 and a wavelength-independent two-way splitter, placed in line. This approach is less costly, although at least half of the optical power will be lost going each way. In addition, an optical isolator could be placed between the tunable VCSEL 30 and the optical circulator 47 if very high suppression of back-reflected light is needed. In this embodiment, the sensor can be a fiber Bragg grating, a planar Bragg grating, a surface plasmon resonance sensor, a Fabry-Perot etalon sensor or a characteristic absorber/reflector sensor.

Additionally in the FIG. 2A embodiment, the light from the tunable VCSEL 30 propagates toward the sensor 45 that is composed of an array of sensors disposed at intervals along the optical fiber 44. Each Bragg grating sensor within sensor array 45 reflects a predetermined narrow wavelength band of light and passes the remaining wavelengths on toward the next sensor. The transmitted beam therefore contains a narrow absorption band corresponding to the reflected band, but the remainder of the light is available to use with the other sensors. The sensors in array 45, in the illustrative embodiment, can be placed in parallel or in series and multiplexed by Wavelength Division Multiplexing (WDM) and/or TDM. WDM is realized by sensors 45 having different central reflection wavelengths, while TDM is realized by intentionally introduced time delays, by any technique known to those skilled in the art, between sensors that may or may not have the same central reflection wavelengths. In this embodiment, the sensors can be fiber Bragg gratings, planar Bragg gratings, surface plasmon resonance sensors, characteristic absorption/reflection sensors or Fabry-Perot etalon sensors.

Figure 2B:
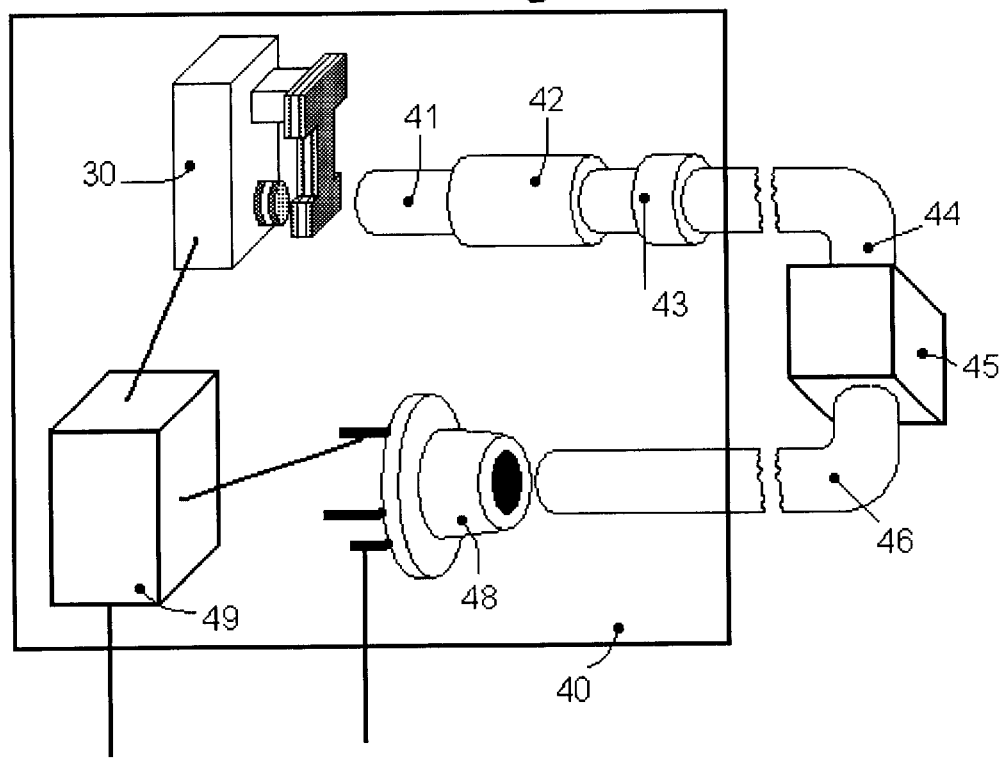
FIG. 2B is a schematic block diagram of a first state of an illustrative, exemplary non-limiting sensor diagnostic system capable of determining the value of static and dynamic physical, chemical or biological stimuli in a transmission mode, employing a tunable VCSEL as an optical excitation source and a photodiode or similar simple device as a detector.

FIG. 2B shows an example illustrative embodiment of a diagnostic system 40 provided in accordance with a second aspect of this invention. FIG. 2B is a schematic block diagram of a first state of an illustrative, exemplary sensor diagnostic system capable of determining the value of static and dynamic physical, chemical or biological stimuli in a transmission mode; necessarily employing a tunable VCSEL as an optical excitation source and a photodiode or similar simple device as a detector Preferred embodiment diagnostic system 40 includes a MEMS-tunable VCSEL 30, a fiber light coupling means 41, an optical isolator 42, a wavelength reference 43, exterior fiber 44 and coupling means to the sensor or sensor array 45, exit fiber 46, a photodetector 48, and a control block 49. In said illustrative example, a tunable VCSEL 30 is assembled with necessary means to fiber couple 41 the emitted light, isolate 42 the VCSEL from back-reflections, provide an accurate wavelength reference 43 and couple the VCSEL assembly 40 to an external fiber 44 to convey the laser light to an optical sensor or sensor array 45 in a transmission mode. An exit optical fiber 46 is provided to couple the optical output transmitted through the sensor or sensor array 45 to the photodetector 48, the electrical signal from which is relayed to the control block circuitry 49 and external electronic circuitry as required. The control block may or may not control the laser temperature via a thermoelectric element or other means and may or may not adjust the laser power output according to a signal from a monitor photodiode 38, as required.

In this embodiment, the sensor array 45 includes individual Bragg gratings that each transmits light having different, non-overlapping, associated amplitude transmission minima at individual transmission wavelengths, spectrally distinguishable one from the other. In the exemplary embodiment, the wavelength position of the amplitude minimum transmitted by each of the Bragg gratings in the array 45 varies in response to a physical stimulus or perturbation imposed on the corresponding sensor. The sensors in array 45, in the illustrative embodiment, can be placed in parallel or in series and multiplexed by Wavelength Division Multiplexing (WDM). TDM is not applicable in this embodiment. Other aspects of this embodiment are the same as in the first embodiment, drawn in FIG. 2A. In this embodiment, the sensors can be fiber Bragg gratings, planar Bragg gratings, surface plasmon resonance sensors, characteristic absorption/reflection sensors or Fabry-Perot etalon sensors.

In preferred embodiments illustrated in FIGS. 2A and 2B, the fiber 44 and the sensor array 45 may be bonded to or embedded in a structure which is being monitored for a perturbation change, such as dynamic or static strain and/or temperature and/or pressure and/or electrical current/or magnetic field. The structure may be made of metal, plastic, composite, or any other materials and the sensors may be disposed on or within the structure.

Signal processing circuits (FIG. 2A, 2B) analyze the electrical signals and provide a plurality of output electrical perturbation signals, indicative of the perturbation being measured by the sensors within the structure. It should be understood that a single line that is time multiplexed or that provides serial digital data for each sensor might also be used.

In the embodiments illustrated in FIGS. 2A and 2B, the wavelength tuning control circuitry in control block 49 may include a function generator in order to produce the control signal waveforms in illustrated in FIGS. 3A–3J. FIGS. 3A–3J are a series of graphs showing exemplary, illustrative time-varying tuning control signals, represented by $V_t$, applied to a tunable VCSEL 30. Output wavelengths, $\lambda$, and the resulting optical power spectrum from the sensors 45 as a function of both time and wavelength in reflection and transmission modes are shown as well. The waveforms shown are a sawtooth waveform (3A–3D), sinusoidal waveform (3E–3H) and triangular waveform (3I, 3J), but many others could be used. It is important to the sensor system operation that the wavelength versus time should be known accurately, and the linear triangle wave (3I, 3J) would be superior from that point of view. The triangle waveform also allows reading all sensors 45 twice per cycle. In the exemplary embodiment, the control signal $V_t$ relates directly to the expansion or contraction of the cavity 38 in the VCSEL 30, thereby causing the wavelength $\lambda$ of the output light to vary in proportion to the applied control signal $V_t$. Thus, the wavelength $\lambda$ of the light varies linearly from $\lambda_1$ to $\lambda_2$, which range includes at least one peak reflection or transmission minimum wavelength $\lambda_b$ from a sensor and optionally at least one peak or minimum from a wavelength reference, which is shown as WR. For the sake of simplicity of the figures, reflection or transmission from just one sensor is shown. Also for simplicity of illustration, the optical power graphs for the triangular wave are not shown, as they are similar to 3C and 3D with the sensor signals occurring twice per cycle.

The triangle waveform (FIG. 3I, 3J), although providing linear dependence of the wavelength vs. time, has the disadvantage of having a discontinuity in the waveform that will by its nature induce higher frequencies, or ringing, into the system. The ringing can be filtered out by various means known in the art, but a penalty is paid in time and efficiency. The sinusoidal control signal will provide frequency stability and power-conserving scanning with much faster scanning rate due to the elimination of the stabilizing time required of a mechanical structure when a discontinuous forcing function is applied, such as the triangle wave. With the sinusoidal waveform, the entire scan can occur in a few microseconds or shorter time. This is two orders onagnitude speed advantage over conventional lasers, allowing better statistical averaging techniques to be used and allowing non-spectral shift sensors (e.g., bandgap semiconductor or other characteristic absorber/reflectors) to be scanned fast enough to minimize optical noise interference. The optical power sensor signals for the sinusoidal waveforms are illustrated schematically in FIGS. 3G and 3H, showing the non-linear nature of the signals in time.

Figure 3A:
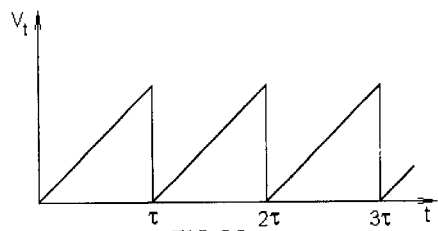
FIGS. 3A–3J are a series of illustrative, exemplary graphs showing time-varying tuning control signals, $V_t$, applied to a tunable VCSEL and the resulting spectral power transmission and/or reflection signals produced by the sensor.
Figure 3B:
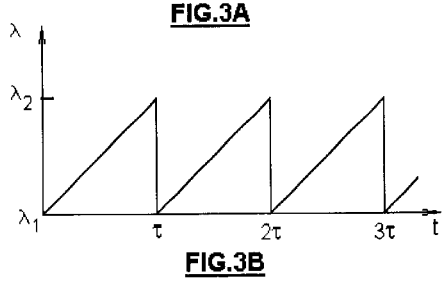
Figure 3E:
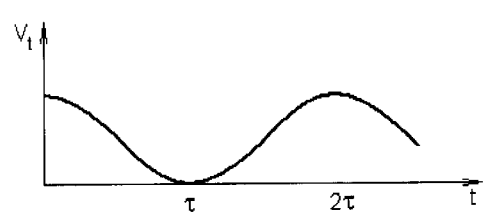
Figure 3F:
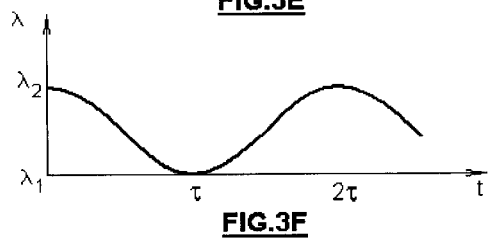
Figure 3C:
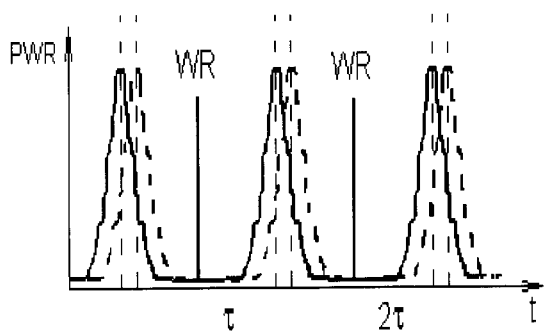
Figure 3G:
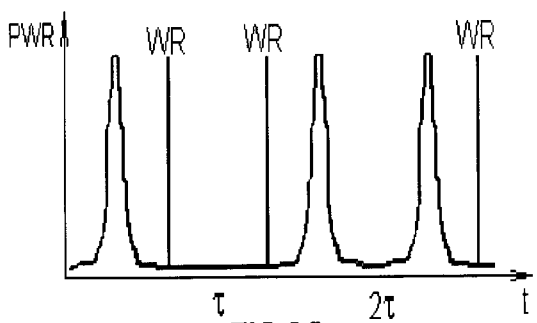
Figure 3D:
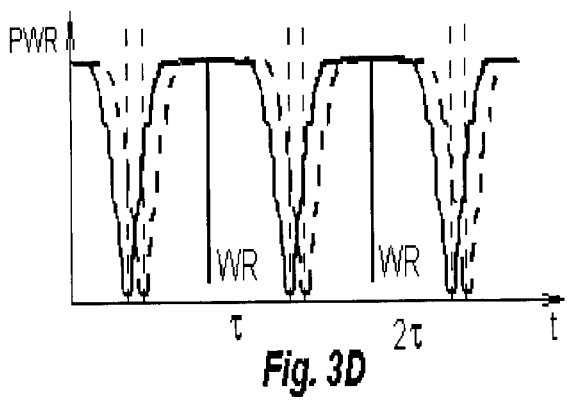
Figure 3H:
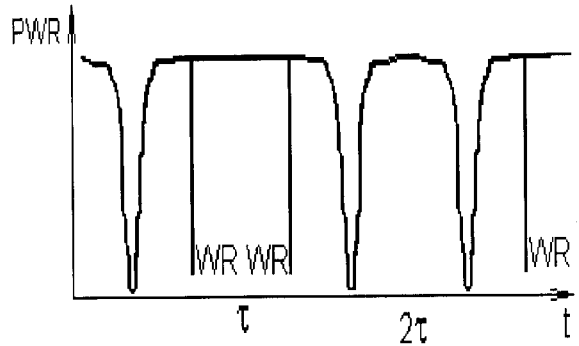
Figure 3I:
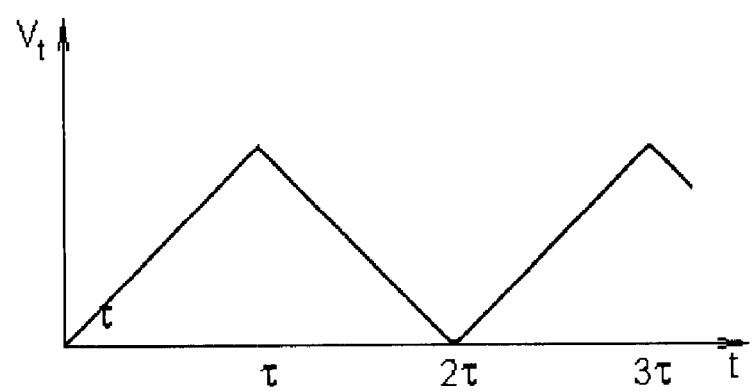
Figure 3J:
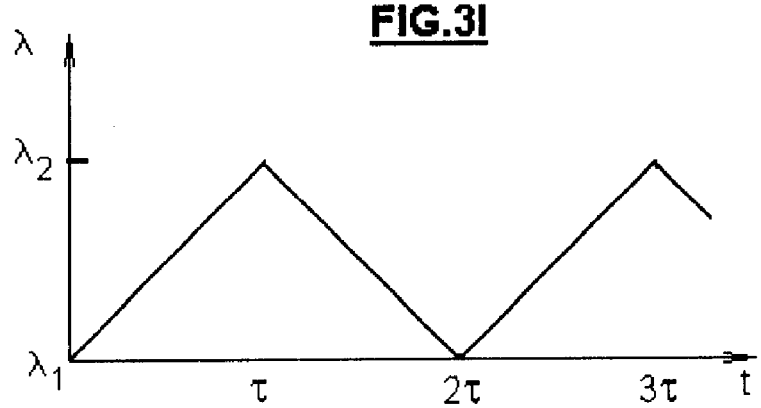

As a result of the scan through the wavelength range, the optical signal at the input to the optical detector 48 as well as the electrical signal from the optical detector will appear as indicated in illustration FIG. 3C or 3G for the reflection mode and FIG. 3D or 3H for the transmission mode. In particular, the electrical signal from the optical detector will experience a sharp increase or decrease respectively (as dictated by sensor design) in power centered at the central wavelength $\lambda_a$ of each sensor. If TDM is also used, the output is somewhat more complex, but know to those skilled in the art. For the sinusoidal drive, the results of a scan are given in FIGS. 3G, 3H.

In the illustrative embodiment, the control block 49, in cooperation with additional signal processing circuitry, determines the static or dynamic value of the sensor stimulus by determining at what wavelengths the maxima or minima in signal level occur and determining the amount of change from the wavelength maximal or minima of the unperturbed sensors. Calibration defines the relationship between a change in the stimulating parameter and a corresponding change in wavelength. The wavelength value is determined by monitoring the wavelength control signal and comparing it to the wavelength reference 43 or mirror 32 position feedback 35(capacitive), as required. Because this signal is directly related to the wavelength of the tunable VCSEL 30, it provides a directly proportional value of the instantaneous wavelength. Many computation algorithms known to those skilled in the art can perform the determination of wavelength position of the minima or maxima. For the illustrative purposes only, one of the possible algorithms is described below. The ability to calculate the position of an extremum from relatively few data points enables enhanced accuracy with lower computational overhead.

During the each full tunable VCSEL wavelength scan N intensity measurement points are taken. Since photodetector 48 and the signal processor in the control block 49 can be made to operate by known art at GHz frequencies, the number N could be adequately large even if the tunable VCSEL could be operated at a maximum tuning speed of tens of kHz. Let us assume that the tunable VCSEL operates at a frequency of only 1 kHz (each scan takes 1 millisecond), which is still two orders of magnitude faster than commonly available from non-MEMS tunable lasers. In this case, at least 100,000 intensity measurements could be taken during each scan. Further assuming the maximum wavelength span of the tunable VCSEL does not exceed 50 nm, intensity measurements could be made every 0.5 picometers. Since communications art has advanced into the tens of GHz and slower scanning speeds can be tolerated in practical situations, greater wavelength resolution could be obtained. Further, since typical Bragg reflection peaks (or transmission minima) wavelength widths are on the order of hundreds of picometers, the embodiments illustrated in FIGS. 2A and 2B are capable of extremely high wavelength resolution. In the embodiment of Bragg gratings employing phase shifts, in which a much narrower peak or valley (20 picometers or narrower) is incorporated inside the primary valley or peak (respectively), the sensor data rate obtainable, as illustrated, will enable several data points to be taken within the phase shift band. This in turn will allow the interpolation of the spectral data from the sensor array by a mathematically smooth, continuous function of time, F(t). F(t) can then be transformed to a function of wavelength, F($\lambda$), according to the type of VCSEL tuning drive used, or directly into a function of the parameter being measured. Many applicable mathematical techniques and their electronic implementations are known in the art. When used, wavelength references can be analyzed in the same manner. Further simple algorithms are used to compute wavelength changes for each sensor by comparison to the previous F($\lambda_s$) and the wavelength reference.

Instead of relying on the tuning control signal or feedback from a cantilever or diaphragm position monitoring means, such as capacitance, to calibrate the VCSEL wavelength against time, an additional unstrained or unperturbed reference means in the form of at least one Bragg grating, Fabry-Perot etalon or absorption cell may be inserted into the optical path at 43. Said reference grating or cell must cause at least one reflection peak or absorption valley within the tuning range and not interfering with any sensor wavelength band, and may provide multiple extrema at $\lambda^{ref\ 1}$, $\lambda_{ref\ 2}$, $\lambda_{ref\ 3}$, . . . $\lambda_{ref\ n}$ that are always located at the same wavelength positions. Knowledge of the predetermined cycle rate, or waveform, of the voltage or other tuning signal, together with such reference wavelengths, provides the signal processing circuit with sufficient information to synchronize the beginning of each new tuning cycle with the laser wavelength. The number of wavelength reference points is determined by the accuracy and linearity of the laser tuning mechanism and the required accuracy of the physical parameter measurement. The fewest reference points will provide the most economical system. In place of a reference Bragg grating or gratings, a number of high finesse Fabry-Perot cavity filters could be used. Another applicable method of maintaining wavelength accuracy would be to place an acetylene cell in the optical path. Acetylene exhibits a number of very sharp absorption peaks in the communications wavelength bands that can be used to calibrate the system on every cycle or every half cycle. Other techniques may also be employed to maintain calibration accuracy to needed levels by those skilled in the art.

Even though the embodiments have been most frequently described as using Bragg gratings as the sensors that detect the environmental stimulus, any reflective or transmittive device having a narrow reflection or transmission wavelength band, or transition slope (e.g., bandgap semiconductors) or any other reflection or transmission spectral peculiarity that shifts with applied perturbation may be used. Some examples of such sensors include Fabry-Perot cavity pressure, temperature and/or displacement sensors, waveguide and surface plasmon resonancebased biological and/or chemical sensors, semiconductor bandgap strain, temperature or pressure sensors and fluorescent and vibronic materials. In the latter two types of materials, the absorption bands are much narrower than that of semiconductors, and they do not have to exhibit fluorescent light output in the spectral range of use.

Figure 4:
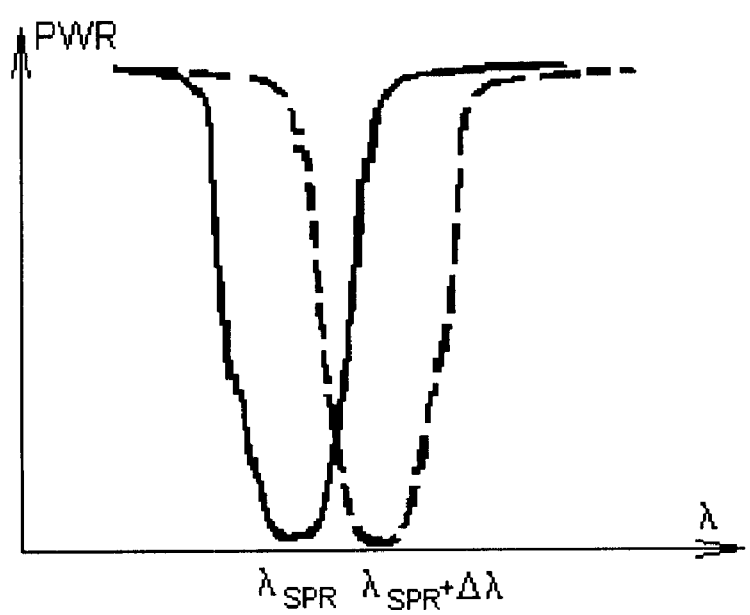
FIG. 4 is a graph of an illustrative, exemplary transmission optical power profile of a sensor employing Surface Plasmon Resonance to produce a shift in the wavelength position of the spectral power minimum in response to a physical, chemical or biological stimulus.

An example of a surface plasmon resonance-based sensor transmission spectrum is given in FIG. 4. The valley in the curve, caused by a surface plasmon, is shifted in wavelength by, for example, a biomass specimen to be detected as it is adsorbed onto the sensor surface. The absolute value of said shift provides very precise information about the concentration of, for example, a reagent in the solution. Additionally, the temporal behavior of said shift can provide information about the kinetics of associated chemical interactions. The high tuning rate of the MEMS-tunable VCSEL enables faster and higher resolution kinetics studies possible, widening the range of applications. The employment of MEMS-tunable VCSEL 30 as a light source will make the afore-described types of sensor systems considerably less expensive and more functional than those employing prior art lasers and/or optical spectrometers and will provide at least an order of magnitude increase in the system resolution through computational and statistical means. Another feature of surface plasmon resonance sensors is that the resonance transmission valley can be located at any predetermined wavelength within the near infrared or infrared spectrum. Thus, tunable VCSELs 30 operated at 950–980 nm, for example, will be equally as useful as VCSELs operating in the communications bands in the 1310 nm and 1550 nm ranges, with little change in cost. This further advantage of tunable VCSEL sensor systems allows a wide variety of sensor types and materials to be matched with a suitable, inexpensive tunable laser. The mathematical algorithm for extracting the position of the wavelength at the minimum of transmission will be similar to the one described for the reflective or tranmissive Bragg grating sensor above. Wavelength multiplexing in this case will be limited by the greater width (typically tens on nanometers) of SPR reflectivity minima and the maximum tuning wavelength span of the tunable VCSEL, possibly as low as two sensors. Time division multiplexing is applicable in this case, as well.

Figure 5A:
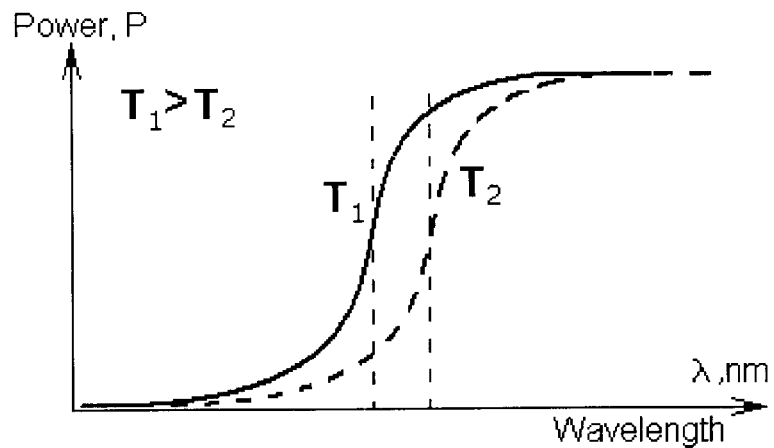
FIG. 5A is an illustrative, exemplary diagram of the spectral power transmission of a characteristic absorber/reflector in the form of a bandgap semiconductor showing a shift in wavelength due to an increase in temperature.

An illustrative example of the transmission spectrum of a semiconductor bandgap absorption-edge temperature sensor is shown in FIG. 5. The bandgap edge wavelength position is a function of the semiconductor temperature according to well-known mathematical and physical formulations. Such an absorption edge is blue-shifted as a whole when the temperature decreases and red-shifted when the temperature increases, as illustrated in FIG. 5A. In this case, which is illustrative of its type, the scanned absorption edge will only yield accurate temperature or pressure data if the scanning process is completed in a much faster time than either the thermal response time of the semiconductor mass or the speed and/or the frequency of absorption-dependent noise (e.g., microbending noise) in the remainder of the fiber circuit. This is because the absorption of the semiconductor cannot be distinguished from absorption noise unless the shape of the edge can be traced out very rapidly. For the greatest accuracy, the spectral shape, undistorted by optical noise, of the absorption curve is required, not the absolute value of the absorption. Thus an advantage of the exceptional tuning speed of the MEMs-tuned VCSEL 30 in this arrangement will make possible inexpensive fiber optic temperature sensors using chips of many semiconductor materials, with or without a mirrored surface, with good sensitivity and adequate accuracy for applications such as microwave ovens. Further, such sensors can be selected to match the desired temperature range and VCSEL properties by using alloy compositions available with continuously varying bandgaps, such as alloys and compounds of indium, aluminum, gallium and arsenic or silicon and germanium.

Figure 5B:
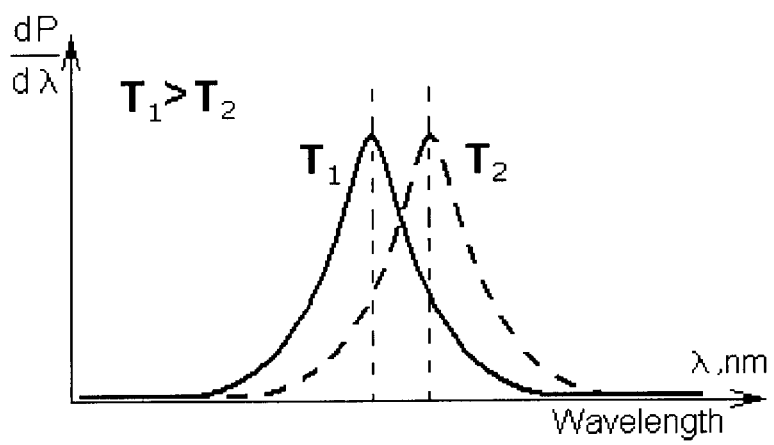
FIGS. 5B and 5C are, respectively, illustrations of the increases in the accuracy of wavelength shift determination with the knowledge of the first and second derivatives of the power transmission spectra.
Figure 5C:
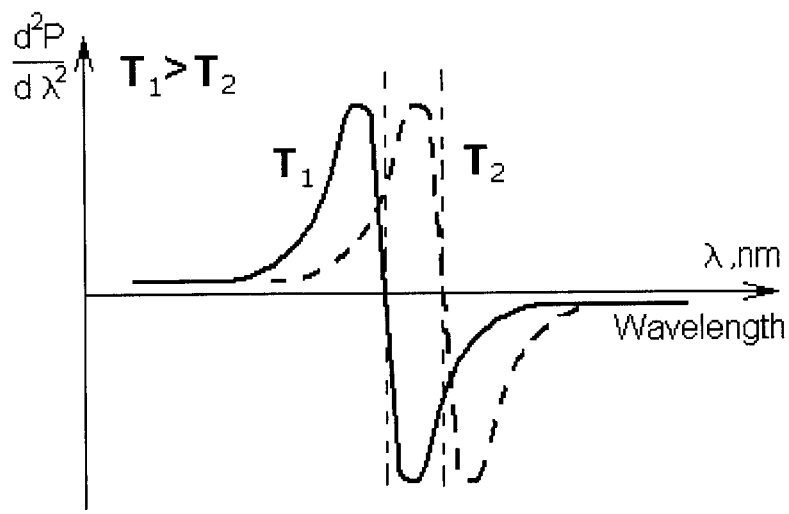

FIGS. 5B and 5C are illustrative examples of improved means of detecting precisely the spectral position of an absorption band with a very wide maximum, such as the "long pass" band of a semiconductor. The "S"-shaped absorption curve can be converted to a peaked curve by taking the first derivative, as shown in FIG. 5B. The computational algorithm for this case is then similar to the cases of Bragg grating sensors and SPR-based sensors described heretofore. This is equally applicable to a single pass of the light through the absorber in transmission, or a double pass through the material if a mirror means is utilized on the output side of the sensor. A second means of accurately determining the amount of wavelength change from the unperturbed wavelength is provided by taking the second derivative of the transmission spectrum, as shown in FIG. 5C, which provides the opportunity to use a "zero crossover" point to define the spectral shift. In the case of a pure semiconductor, the sensors will be self-calibrating since the wavelength dependence of the absorption edge is very well known. In the case of alloys, calibration may be performed. Many computation algorithms known to those skilled in the art can perform the determination of wavelength position utilizing the peak of the first derivative or the zero crossing of the second derivative. The spectra can be interpolated, smoothed or subjected to any other mathematical analysis known to those skilled in the art.

Referring to Bragg grating sensors, the sensors 45 need not be written into the same type of fiber 44 as the fiber that feeds the sensors, e.g., the sensors can be spliced into the fiber 44 or they can be separate planar chips, optically coupled to the fiber by means commonly known in the art.

Further, the embodiments have been described as employing an optical fiber 44, but any other form of optical waveguide may be used if desired.

Also, it should be understood that the tuning control circuit 49 and subsequent signal processing can be done with any degree of combination of software and hardware by many methods known in the art.

Although the invention has been described and illustrated with respect to the exemplary embodiments thereof, it should be understood by those skilled in the art that the foregoing and various other changes, omissions and additions may be made without departing from the scope of the invention.

We claim:

1. An optical sensor diagnostic system, comprising:

a tunable VCSEL incorporating an integrated MEMS wavelength tuner for providing wavelength-tunable light in response to a tuning control signal, said tunable light being launched into an optical waveguide, said tunable VCSEL including a movable tuning mirror and a capacitive or optical detector for detecting the position of the movable tuning mirror and providing feedback;

at least one optical sensor, disposed in the path of said tunable light, said at least one sensor providing a transmitted light having at least one associated characteristic amplitude feature selected from the group consisting of a minimum, a maximum or a slope located at a particular wavelength within the transmitted wavelength range, said wavelength at each minimum, maximum or sloped transmission amplitude being responsive to an environmental stimulus imposed upon said at least one sensor;

said tunable VCSEL individually illuminating said at least one sensor in a wavelength range spanning said wavelength location of said associated characteristic transmission amplitude feature;

an optical isolator, disposed in the path of said tunable light between said tunable VCSEL and said at least one sensor, for isolating said tunable light source from light reflected from said at least one sensor;

an optical detector, disposed in the path of said transmitted light, for detecting said transmitted light from said at least one sensor and for providing an electrical detection signal indicative of the power of said transmitted light throughout a predetermined wavelength range;

a controller for providing a variable tuning control signal to said tunable VCSEL indicative of the desired wavelength of said tunable light;

at least one wavelength reference independent of said tuning control signal and moveable mirror position detector disposed in the path of the light; and a signal processor responsive to said electrical detection signal, for detecting a wavelength defined on the characteristic transmission amplitude feature in order to quantitatively detect the effect on said at least one sensor due to said environmental stimulus, changes in said wavelength at the characteristic transmission amplitude feature caused by changes in said environmental stimulus, and for providing a signal indicative of said stimulus or change therein.

2. The optical sensor diagnostic system of claim 1 wherein said at least one sensor comprises plural wavelength division multiplexed optical sensors.

3. The optical sensor diagnostic system of claim 1 wherein said at least one sensor comprises plural time division multiplexed optical sensors.

4. The optical sensor diagnostic system of claim 1 wherein said at least one sensor comprises an environment reference or compensation sensor.

5. The optical sensor diagnostic system of claim 1 wherein said detection and signal processor comprises a tracker, responsive to said electrical detection signal, for adjusting a voltage or other control signal to allow said tunable light to track static and dynamic values of said characteristic transmission amplitude feature for said at least one sensor, thereby providing utilization of the control signal as the output characteristic of the physical stimulus, making unnecessary scanning of the complete wavelength range and greatly increasing the speed of data acquisition.

6. The optical sensor diagnostic system of claim 1 wherein said controller comprises a modulator for modulating said voltage control signal at a predetermined modulation frequency.

7. The optical sensor diagnostic system of claim 1 wherein said signal processor comprises a demodulator operating at said modulation frequency, for demodulating said electrical detection signal and for providing a demodulated signal indicative thereof.

8. The optical sensor diagnostic system of claim 1 wherein said signal processor incorporates a computational element for increasing the accuracy and precision of determining the wavelength position of said characteristic transmission amplitude feature and changes therein for each of said sensor.

9. The optical sensor diagnostic system of claim 1 wherein:
said at least one sensor comprises plural sensors;
said controller comprises a scanner that scans said control signal for the purpose of causing said tunable VCSEL to scan its wavelengths across said characteristic transmission amplitude features of said plural sensors; and
said signal processor determines, in response to said voltage or other control signal, the wavelength of said tunable light from the magnitude of said voltage or other control signal and/or mirror position feedback signal and for determining which of said plural sensors is being illuminated, thereby determining the value of the environmental stimulus at the position of said illuminated sensor.

10. The optical sensor diagnostic system of claim 1 wherein:
said at least one sensor comprises plural sensors;
said controller comprises a scanner that scans said control signal so as to cause said tunable VCSEL to scan across the characteristic transmission amplitude features of said plural sensors and for providing a synchronization signal indicative of when said voltage control signal begins and ends said scanning; and
said signal processor determines, in response to said synchronization signal, which of said plural sensors is being illuminated, thereby determining changes in said wavelength at said characteristic transmission amplitude feature.

11. The optical sensor diagnostic system of claim 1 wherein said at least one sensor comprises at least one fiber or planar Bragg grating.

12. The optical sensor diagnostic system of claim 1 wherein said at least one sensor includes at least one Bragg grating that incorporates phase shift in its structure, said phase shift producing a sharper maximum within said transmitted wavelength band minimum.

13. The optical sensor diagnostic system of claim 1 wherein said at least one sensor comprises at least one Fabry-Perot etalon.

14. The optical sensor diagnostic system of claim 1 wherein said at least one sensor comprises at least one Surface Plasmon Resonance structure.

15. The optical sensor diagnostic system of claim 1 wherein said at least one sensor comprises at least one thin film or bulk material characteristic absorber material.

16. The system of claim 15 wherein characteristic absorber material comprises one or more vibronic, excitonic or fluorescent materials.

17. The optical sensor diagnostic system of claim 1 wherein said environmental stimulus comprises any combination of mechanical stress, temperature, pressure, electrical current, electrical field, magnetic field or chemical or biological material on said sensor.

18. The optical sensor diagnostic system of claim 1 wherein at least one wavelength reference, not affected by any environmental stimulus, comprising at least one of the group of a Bragg grating, a phase shift Bragg grating, a Fabry-Perot etalon or a gas-containing chamber, is disposed in the optical path.

19. The optical sensor diagnostic system of claim 1 wherein the wavelength reference comprises at least one gas-containing chamber containing acetylene gas.

20. An optical sensor diagnostic system, comprising:
a VCSEL incorporating integrated MEMS wavelength tuner for providing wavelength-tunable light in response to a tuning control signal, said tunable light being launched into an optical waveguide, wherein is provided
at least one optical sensor, disposed in the path of said tunable light, each providing a reflected light having at least one associated characteristic amplitude feature from but, not limited to, the group, a minimum, a maximum or a slope located at a particular wavelength within the reflected wavelength range, said wavelength at each minimum, maximum or sloped reflection amplitude being responsive to an environmental stimulus imposed upon a corresponding sensor;
said tunable VCSEL for individually illuminating each of said sensor in a wavelength range spanning said wavelength location of said associated characteristic reflection amplitude feature;
optical detector, disposed in the path of said reflected light, for detecting said reflected light from each of said sensor and for providing an electrical detection signal indicative of the power of said reflected light throughout the appropriate wavelength range;
optical circulator, disposed in the path of said tunable light between said tunable VCSEL and said sensor, for isolating said tunable light source from light reflected from said sensor and directing the light to said detector;
voltage or other controller for providing a variable tuning control signal to said tunable VCSEL indicative of the desired wavelength of said tunable light;
capacitive or optical detector that detects the position of the movable tuning mirror and providing feedback; and
at least one wavelength reference independent of said tuning control signal and moveable mirror position detector disposed in the path of the light, and
signal processor responsive to said electrical detection signal, for detecting a wavelength defined on the characteristic reflection amplitude feature in order to quantitatively detect the effect on said sensor due to said environmental stimulus, changes in said wavelength at the characteristic reflection amplitude feature caused by changes in said environmental stimulus, and for providing a signal indicative of said stimulus or change therein for each of said sensor.

21. The optical sensor diagnostic system of claim 20 wherein said optical sensors are wavelength division multiplexed.

22. The optical sensor diagnostic system of claim 20 wherein said optical sensors are time division multiplexed.

23. The optical sensor diagnostic system of claim 20 wherein at least one of said sensors serves as an environment reference or compensation sensor.

24. The optical sensor diagnostic system of claim 20 wherein said detection and signal processor comprises tracker, responsive to said electrical detection signal, for adjusting said voltage or other control signal to allow said tunable light to track static and dynamic values of said characteristic reflection amplitude feature for each of said sensor, thereby providing utilization of the control signal as the output characteristic of the physical stimulus, making unnecessary scanning of the complete wavelength range and greatly increasing the speed of data acquisition.

25. The optical sensor diagnostic system of claim 20 wherein said voltage controller comprises a modulator for modulating said voltage control signal at a predetermined modulation frequency.

26. The optical sensor diagnostic system of claim 20 wherein said signal processor comprises a demodulator operating at said modulation frequency, for demodulating said electrical detection signal and for providing a demodulated signal indicative thereof.

27. The optical sensor diagnostic system of claim 20 wherein said signal processor performs computations that increase the accuracy and precision of determining the wavelength position of said characteristic reflection amplitude feature and changes therein for each of said sensor.

28. The optical sensor diagnostic system of claim 20 wherein:
said voltage or other controller comprises a scanner that scans said voltage control signal so as to cause said tunable VCSEL to scan its wavelength across said characteristic reflection amplitude feature of any or all of said sensor; and
said signal processor determines, in response to said voltage or other control signal, the wavelength of said tunable light from the magnitude of said voltage or other control signal and/or mirror position feedback signal and for determining which of said sensor is being illuminated, thereby determining the value of the environmental stimulus at the position of said individual sensor.

29. The optical sensor diagnostic system of claim 20 wherein:
said voltage or other controller comprises a scanner that scans said voltage control signal so as to cause said tunable VCSEL to scan across the wavelengths of the characteristic reflection features of all of said sensor; and for providing a synchronization signal indicative of when said voltage control signal begins said scanning; and
said signal processor determines, in response to said synchronization signal, which of said sensor is being illuminated, thereby determining changes in said wavelength at said characteristic reflection amplitude feature.

30. The optical sensor diagnostic system of claim 20 wherein said at least one sensor comprises at least one fiber or planar Bragg grating.

31. The optical sensor diagnostic system of claim 30 wherein at least one Bragg grating of at least one sensor comprises at least one incorporated phase shift in its structure, said phase shift producing a sharper minimum within said reflected wavelength band maximum.

32. The optical sensor diagnostic system of claim 20 wherein said at least one sensor comprises at least one Fabry-Perot etalon.

33. The optical sensor diagnostic system of claim 20 wherein said at least one sensor comprises at least one Surface Plasmon Resonance structure.

34. The optical sensor diagnostic system of claim 20 wherein at least one sensor is disposed in a branch waveguide or optical fiber coupled to the main trunk waveguide by a coupler.

35. The optical sensor diagnostic system of claim 34 wherein said at least one sensor comprises at least one thin film or bulk material characteristic absorber material.

36. The characteristic absorber material of claim 35 comprising at least one semiconductor.

37. The characteristic absorber material of claim 36 chosen from the full possible range of alloys and compounds of zinc, cadmium, mercury, silicon, germanium, tin, lead, aluminum, gallium, indium, bismuth, nitrogen, oxygen, phosphorus, arsenic, antimony, sulfur, selenium and tellurium.

38. The characteristic absorber material of claim 35 comprises one or more vibronic, excitonic or fluorescent materials.

39. The characteristic absorber material of claim 35 wherein said sensor comprised of said characteristic absorber material incorporates a mirror at the distal end, providing signal reflection by double-pass transmission.

40. The optical sensor diagnostic system of claim 20 wherein at least one sensor produces a characteristic absorption feature in the form of a slope, wherein:
the said wavelength indicative of the characteristic absorption slope is determined by taking the first derivative of the light amplitude with respect to the wavelength, and by analytically extracting the wavelength position of resulting said first wavelength derivative extremum, or, alternatively,
the said wavelength indicative of the characteristic absorption slope is determined by taking the second derivative of the light amplitude with respect to the wavelength and by analytically extracting the wavelength positions of said second wavelength derivative zeros.

41. The optical sensor diagnostic system of claim 20 wherein said environmental stimulus is any combination of mechanical stress, temperature, pressure, electrical current, electrical field, magnetic field or chemical or biological material on said sensors.

42. The optical sensor diagnostic system of claim 20 wherein at least one wavelength reference, not affected by any environmental stimulus, comprising at least one of the group of a Bragg grating, a phase shift Bragg grating, a Fabry-Perot etalon or a gas-containing chamber, is disposed in the optical path.

43. The optical sensor diagnostic system of claim 42 wherein the gas-containing chamber contains acetylene gas.

44. The optical sensor diagnostic system of claim 20 wherein a said sensor comprising an optical fiber having a core waveguide and a cladding or cladding/buffer layer surrounding the core waveguide, in addition incorporating an input/output end and a terminal reflection end, wherein the terminal reflection end is defined by an end face of the core waveguide in contact with a mirrored layer such that the light is caused to reverse its direction of propagation and exits the input/output end, said sensing area is defined by a surface of the optical fiber core waveguide free from the surrounding cladding or cladding/buffer layer.

45. The optical sensor diagnostic system of claim 44 wherein the said sensing area further contains at least one additional functional layer adhered to the surface plasmon resonance-supporting metal layer.

46. The optical sensor diagnostic system of claim 45 wherein the at least one additional layer comprises a chemically reactive layer.

47. The optical sensor diagnostic system of claim 45 wherein the at least one additional layer comprises a biologically reactive layer.

48. The optical sensor diagnostic system of claim 44 wherein the said plasmon resonance supporting metal is one or more layers of elements or alloys chosen from the group silver, gold, copper or aluminum.

49. The optical fiber sensor according to claim 44 further incorporating a polarizer positioned anywhere between said tunable VCSEL and said sensor, said polarizer selecting light with polarization P.

50. The optical fiber sensor according to claim 45 further comprising a first polarizer positioned between the said tunable VCSEL and said circulator, said polarizer selecting light with polarization state between S and P polarizations.

51. The optical fiber sensor according to claim 50 further comprising a second polarizer positioned between the said sensor and said detector, said second polarizer being oriented with respect to the said first polarizer such that a phase-polarization enhancement is obtained of the ratio of the power amplitudes at wavelengths outside the said minimum of reflection feature to the power amplitude at the exact minimum of reflection.

* * * * *